United States Patent [19]
Pierschbacher et al.

[11] Patent Number: 5,955,578
[45] Date of Patent: *Sep. 21, 1999

[54] POLYPEPTIDE-POLYMER CONJUGATES ACTIVE IN WOUND HEALING

[75] Inventors: Michael D. Pierschbacher, San Diego; James W. Polarek, Del Mar; Marianne P. Petrica, San Diego; Erkki I. Ruoslahti, Rancho Santa Fe, all of Calif.

[73] Assignee: La Jolla Cancer Research Foundation, La Jolla, Calif.

[*] Notice: This patent is subject to a terminal disclaimer.

[21] Appl. No.: 08/463,835

[22] Filed: Jun. 5, 1995

Related U.S. Application Data

[63] Continuation of application No. 08/383,616, Feb. 2, 1995, abandoned, which is a continuation of application No. 08/013,154, Feb. 1, 1993, abandoned, which is a division of application No. 07/978,054, Nov. 18, 1992, abandoned, which is a continuation of application No. 07/286,973, Dec. 20, 1988, abandoned.

[51] Int. Cl.$^6$ .................................................. A61K 38/00
[52] U.S. Cl. ............................. 530/345; 514/2; 514/12; 514/21; 530/324; 530/353; 530/354; 530/355; 530/356; 530/357; 530/404; 530/405; 530/408; 530/409
[58] Field of Search .................................. 514/12–18, 8, 514/21; 530/24–330, 345, 353, 354, 356, 357, 404, 405, 408, 409

[56] References Cited

U.S. PATENT DOCUMENTS

| | | | |
|---|---|---|---|
| 3,883,393 | 5/1975 | Knazek et al. | 435/240.24 |
| 4,511,653 | 4/1985 | Play et al. | 435/68.1 |
| 4,517,686 | 5/1985 | Ruoslahti et al. | 436/501 |
| 4,578,079 | 3/1986 | Ruoslahti et al. | 623/11 |
| 4,589,881 | 5/1986 | Ruoslahti et al. | 623/11 |
| 4,614,517 | 9/1986 | Ruoslahti et al. | 623/11 |
| 4,661,111 | 4/1987 | Ruoslahti et al. | 623/501 |
| 4,683,291 | 7/1987 | Zimmerman et al. | 530/324 |
| 4,703,108 | 10/1987 | Silver et al. | 530/356 |
| 4,789,734 | 12/1988 | Pierschbacher | 530/395 |
| 4,792,525 | 12/1988 | Ruoslahti et al. | 435/240.243 |
| 4,857,508 | 8/1989 | Adams et al. | . |
| 4,973,466 | 11/1990 | Reich | 424/426 |
| 5,041,380 | 8/1991 | Ruoslahti et al. | 435/240.2 |
| 5,654,267 | 8/1997 | Vuori et al. | 514/2 |
| 5,677,276 | 10/1997 | Dickerson et al. | 514/8 |
| 5,830,504 | 11/1998 | Vuori et al. | 424/484 |

FOREIGN PATENT DOCUMENTS

| | | |
|---|---|---|
| 142192 | 5/1984 | European Pat. Off. . |
| 341915 | 11/1989 | European Pat. Off. . |
| 63/264069 | 10/1988 | Japan . |
| 1279836 | 11/1989 | Japan . |
| 88/03151 | 5/1988 | WIPO . |
| 88/03810 | 6/1988 | WIPO . |

OTHER PUBLICATIONS

Bedell et al., "Structural requirements for opioid activity of analogues of the enkephalins," *Proc. R. Soc. Lond.*, B. 198:249–265 (1977).

Abstract of Bedell et al., "Structural requirements for opioid activity of analogues of the enkephalins," *Proc. R. Soc. Lond.*, B. 198:249–265 (1977).

Pierschbacher et al., "An adhesion variant of the MG–63 osteosarcoma cell line displays an osteoblast–like phenotype." *Ciba Foundation Syposium*, 136:131–141 (1988).

Pierschbacher, M.D. and Ruoslahti, E. "Influence of Stereochemistry of the Sequence Arg–Gly–Asp–Xaa on Binding Specificiy in Cell Adhesion." *J. Biol. Chem.* 262:17294–17298 (1987).

Beddell et al., "Structural requirements for opioid activity of analogues of the enkephalins" *Proc. R. Soc. Lond. B.* 198:249–265 (1977).

Engvall et al., "Affinity chromatography of collagen on collagen–binding fragments of fibronectin" *Collagen Rel. Res.* 1:505–516 (1981).

Hynes, R.O., "Fibronectins: A family of complex and versatile adhesive glycoproteins derived from a single gene", The Harvey Lectures, Series 81, at page 134 (1987).

Lam et al., "Evidence that arginyl–glycyl–aspartate peptides and fibrinogen α chain petides share a common binding site on platelets" *J. Biol. Chem.* 262:947 (1987).

Grinnell et al., *cell* 19:517–525 (1980).

Bernard et al., *Biochem.* 22:5213–5223 (1983).

Kohno et al., *J. Biol. Chem.* 259(22):13668–13673 (1984).

Seyer et al., *Biochem.* 20:2621–2627 (1981).

Babel et al., *Euro J. Biochem.* 143:545–556 (1984).

Pierschbacher et al., "Synthetic peptide with cell attachment activity of fibronetin" *Proc. Natl. Acad. Sci.* 80:1224–1227 (1983).

Hynes et al., "Cell surface fibronectin and oncogenic transformation," *J. Supramolecular Structure* 11:95–104 (1979).

Hahn et al., "Isolation and biological characterization of active fragments of the adhesive glycoprotein fibronection," *Cell* 18:1043–1051, (1979).

Sekiguchi et al., "Functional domain structure of fibronection," *Proc. Natl. Acad. Sci.* 77:2661–2665 (1980).

Grinnell et al., "Distribution of fibronectin during wound healing in Vivo," *J. Invest. Dermatol.* 76:181–189 (1981).

Mustoe et al., Accelerated healing of incisional wounds in rats induced by transforming growth factor–beta, *Science* 1333–1336 (1987).

Danilov et al., *Expt. Cell Res.* 182:186–196 (1989).

Pierschbacher et al., *Nature* 309:30–33 (1984).

(List continued on next page.)

*Primary Examiner*—Ponnathapura Achutamurthy
*Attorney, Agent, or Firm*—Campbell & Flores

[57] ABSTRACT

A conjugate of a synthetic polypeptide containing RGD or (dR) GD and a biodegradable polymer, such as hyaluronic acid or chondroitin sulfate is disclosed. Methods of making the conjugate and using it to aid wound healing by providing a temporary matrix are disclosed.

10 Claims, 4 Drawing Sheets

OTHER PUBLICATIONS

Pytela et al., *Science* 31:1559–1561 (1986).

Singer et al., *J. Cell Biol.* 104:573–584 (1987).

Suzuki et al., *J. Biol. Chem.* 262(29):14080–14085 (1987).

Plow et al., *Proc. Natl. Acad. Sci.* (USA) 82:8057–8061 (1985).

McDonagh et al., "Amino acid sequence of the factor $XIII_a$ acceptor site in bovine plasma fibronectin," *Febs Letters* 127:174–178 (1981).

Ruoslahti et al., "Alignemnt of biologically active domains in the fibronectin molecule," *J. Biol. Chem.* 256:7277–7281 (1981).

Pande et al., "Comparative structural studies of human plasma and amniotic fluid fibronectins," *Bioch. Biophy. Res. Comm.* 101:265–272 (1981).

Pande et al., "$NH_2$–terminal sequences of DNA–, heparin–, and gelatin–binding tryptic fragments from human plasma fibronectin," *Arch. Bioch. Biophy.* 213:258–265 (1982).

Pierschbacher et al., "The cell attachment domain of fibronectin," *J. Biol. Chem.* 257:9593–9597 (1982).

Seitz et al., "Effect of fibronectin on the adhesion of an established cell line to a surface reactive biomaterial," *J. Biomed. Mat. Res.* 16:195–207 (1982).

Vibe–Pedersen et al., "Amino acid sequence of a peptide from bovine plasma fibronectin containing a free sulfhydryl group (cysteine)," *Febs. Letters* 142:26–30 (1982).

Sekiguchi et al., "Monoclonal antibodies directed to two different domains of human plasma fibronectin: Their specificities", *Fed. Eur. Bich. Soc.* 142:243–246 (1982).

Ehrismann et al., "Arrangement of attachment–promoting, self–association, and heparin–binding sites in horse serum fibronectin", *J. Biol. Chem.* 257:7381–7387 (1982).

Clark et al., "Fibronectin is produced by blood vessels in response to injury", *J. Exp. Med.* 156:646–651 (1982).

Hynes et al., "Fibronectins: Multifunctional modular glycoproteins", *J. Cell. Biol.* 95:369–377 (1982).

Petersen et al., "Partial primary structure of bovine plasma fibronectin: Three types of internal homology", *Proc. Natl. Acad. Sci.* 80:137–141 (1983).

Grinnell, F., "Cell attachment and spreading factors" in *Growth and Maturation Factors* (Dr. Gordon Guroff, Ed.) John Wiley & Sons, Inc., (1983).

Grinnell, F., "The role of fibronectin in the bioreactivity of material surfaces" in *Biocompatible Polymers, Metal, and Composites* (Ed. Michael Szycher), Technomic Publishing, Lancaster, Pennsylvania (1983)

Hayashi et al., "Domain structure of the carboxyl–terminal half of human plasma fibronectin" *J. Biol. Chem.* 258:3332–3340 (1983).

Kornblihtt, et al., "Isolation and characterization of cDNA clones in human and bovine fibronectins" *Proc. Natl. Acad. Sci.* 80:3218–3222(1983).

Ruoslahti et al., "Fibronectin: Current concept of its structure and functions" *Coll. Res.* 1:95–128 (1981).

Engvall et al., "Binding of soluble form of fibroblast surface protein, fibronection, to collagen" *Int. J. Cancer* 20:1–5 (1977).

Ruoslahti et al., "Interaction of fibronection with antibodies and collagen in radioimmunoassay" *Biochimica et Biophysica Acta* 534:210–218 (1978).

Engvall et al., "Nonhelical, fibronectin–binding basement–membrane collagen from endodermal cell culture" *cell* 29:475–482 (1982).

POLYPEPTIDE-POLYMER CONJUGATES ACTIVE IN WOUND HEALING

This application is a continuation of Application Ser. No. 08/383,616, filed Feb. 2, 1995, now abandoned, which is a continuation of Application Ser. No. 08/013,154, filed Feb. 1, 1993, now abandoned, which is a divisional of Application Ser. No. 07/978,054, filed Nov. 18, 1992, now abandoned, which is a continuation of Application Ser. No. 07/286,973, filed Dec. 20, 1988, now abandoned.

The present invention relates to peptides conjugated to biodegradable polymers and methods for using the conjugates to promote the healing of wounds in mammals, including humans.

BACKGROUND OF THE INVENTION

The slow healing or lack of healing of both dermal wounds, such as decubitus ulcers, severe burns and diabetic ulcers and eye lesions, such as a dry eye and corneal ulcer, is a serious medical problem, affecting millions of individuals and causing severe pain or death in may patients. Even the healing of surgical wounds is a problem, particularly in aging and diabetic individuals. Although wounds may be quite dissimilar in terms of cause, morphology and tissue affected, they share a common healing mechanism. Each repair process ultimately requires that the correct type of cell migrate into the wound in sufficient numbers to have an effect: macrophages to debride wounds, fibroblasts for the formation of new collagen and other extracellular matrix components in wounds where the extracellular matrix was damaged, capillary endothelial cells to provide the blood supply, and epithelial cells to ultimately cover the wound.

The unwounded dermis owes much of its structure and strength to the interactions of cells with the extracellular matrix. This matrix contains several proteins known to support the attachment of a wide variety of cells. These proteins include fibronectin, vitronectin, thrombospondin, collagens, and laminin. Although fibronectin is found at relatively low concentrations in unwounded skin, plasma fibronectin deposition occurs soon after wounding. When tissue is damaged, the extracellular matrix must be replaced to provide a scaffold to support cell attachment and migration.

In addition to providing a scaffold, extracellular matrices can also direct cellular proliferation and differentiation. An extracellular matrix can, therefore, direct healing of a tissue in such a way that the correct tissue geometry is restored. When applied to wounds, exogenous fibronectin results in increased wound healing, epithelial migration and collagen deposition. However, a number of considerations, including cost, availability, and instability, make fibronectin or other extracellular matrix proteins less than ideal for such treatment. Moreover, being blood derived products, extracellular matrix proteins may be vectors for infectious disease.

In addition to treatment with fibronectin, attempts have also been made to promote healing by providing cell growth factors such as fibroblast growth factor (FGF) or epidermal growth factor (EGF). Such factors will undoutedly become useful in treating wounds, but because they cannot effect the correct geometry of the new tissue, they can lead to an overly vascularized tissue and abnormal healing.

It is now recognized that the binding domain of fibronectin and the other adhesion proteins is localized in the amino acid sequence Arg-Gly-Asp-X (also termed RGD-X, in accordance with the standard one letter abbreviations for the amino acids) wherein X can be various amino acids or substituents such that the peptide has cell adhesion promoting activity. Arg-Gly-Asp containing peptides and their uses are disclosed, for example, in the following issued United States patents and pending patent applications: U.S. Pat. Nos. 4,578,079 and 4,614,517; Ser. Nos. 744,981 and 738,078. From these discoveries, work has progressed in the generation of various Arg-Gly-Asp containing peptides having various specificities for particular cell surface receptors.

There thus exists a need for an effective agent to promote cell migration and attachment to the site of a wound. Preferably, such an agent should be inexpensive, sterile and have long lasting stability and effectiveness. The present invention satisfies these needs and provides related advantages as well.

SUMMARY OF THE INVENTION

The present invention provides Arg-Gly-Asp containing peptide-polymer conjugates that are useful in promoting rapid healing of wounds and methods for using the peptide-polymer conjugates to treat wounds. In one embodiment, the conjugate comprises a peptide containing the amino acid sequence Y-Gly-Asp wherein Y is Arg or D-Arg attached to the biodegradable polymer. Examples of such polymers include hyaluronate, chondroitin sulfate, heparin, heparan sulfate, polylactate, polyglycolic acid, starch or collagen.

In another aspect, a method of conjugating the peptide to biodegradable polymers is provided. In a further aspect, the invention comprises methods of treating wounds by applying Y-Gly-Asp containing peptide conjugates.

DETAILED DESCRIPTION OF THE INVENTION

The extracellular matrix of mammalian dermis contains several proteins known to support the attachment and promote the migration and differentiation of a wide variety of cells, including fibronectin, vitronectin, collagens and laminin. When the dermis is cut, burned or abraded, this extracellular matrix may be separated or lost. This matrix must be replaced before the wound can be repaired by cellular migration and replication because cells require the matrix to be in place before cell migration, and healing, can occur.

In natural wound healing, the tissue is replaced through the migration of cell and the synthesis of extracellular matrix by them. This process is time-consuming, often requiring more than one year to complete, and results in scarring and a tissue which is weaker than the surrounding, unwounded tissue.

The present invention provides stable "synthetic matrices" that can be used to support the healing of many different wounds by providing the cells with an attachment base for cell migration.

The "synthetic matrix" comprises a conjugate of a biodegradable polymer and a peptide sequence that dermal cells can use as a binding site during migration. Preferably, the peptide contains the sequence Arg-Gly-Asp or D-Arg-Gly-Asp. For dermal wounds, these two components will preferably form a viscous semi-gel, comprising the peptide coupled to a hydrated matrix. The semi-gel is placed directly in the wound at the site or sites of matrix destruction. The wound is otherwise treated in a normal manner. As a semi-gel, the conjugate does not tend to migrate away from the wound site, either due to physical effects such as movement by the patient or by absorption by the patient's own system. The conjugate acts as a temporary replacement matrix that encourages cell migration into the wound and speeds healing. As the wound heals, the conjugate is slowly broken down by the migrating cells and replaced by natural replacement matrix, as evidenced by Example VI. For other applications, such as with corneal abrasion caused by the dry eye condition or other circumstances, a conjugate consisting of an Y-Gly-Asp peptide coupled to chondroitin sulfate is preferable. This conjugate binds to expose dermis collagen matrix, providing attachment sites for corneal epithelial cells. Such material can be provided in liquid form, such as eye drops.

The following standard abbreviations are used herein to identify amino acid residues.

TABLE I

| Amino Acid | Three-letter Abbreviation | One-letter Symbol |
|---|---|---|
| Alanine | Ala | A |
| Arginine | Arg | R |
| D-Arginine | D-Arg | dR |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V | nMe refers to an n-Methyl group.

A portion of the preferred amino acid sequences of the present invention is derived from that of fibronectin. Fibronectin is a naturally occurring protein that is present in low levels in undamaged dermis and in higher levels in damaged dermis. Fibronectin has been shown to be an important factor in healing, because it provides a binding site for migrating cells coming in to replace cells lost due to injury. The amino acid sequence in fibronectin required for cell bonding is Arg-Gly-Asp-X where X is Serine. However, X can be other amino acids or substituents such that the peptide has cell-attachment promoting activity. (Pierschbacher and Ruoslahti, Proc. Natl. Acad. Sci. USA 81:5985–5988 (1984)). Arg-Gly-Asp is also a cell attachment promoting sequence in a number of other adhesive proteins including vitronectin, collagen, fibrin and tenascin. Synthetic peptides containing the sequence are capable of promoting cell attachment when they are presented as an insoluble substrate as well as inhibiting cell attachment to fibronectin or other adhesive proteins when in solution. Several receptors for this peptide sequence have been identified in various cell types (Pytela et al., Cell 40:191–198 (1985); Ruoslahti and Pierschbacher, Science 238:491–497, (1987)). Depending on the type of cell to be attached, the Arg-Gly-Asp-X sequences may be modified to bind preferentially to individual receptors and, therefore, can attract individual types of cells (Pierschbacher and Ruoslahti, J. Biol. Chem. 262:14080–14085 (1987)). In addition, most extracellular matrix proteins contain a basic "heparin-binding" region which appears to enhance all adhesion. This quality can be mimicked by polyarginine, polylysine or polyornithine, or by other basic residues. Moreover, the peptide can be linear or cyclic.

Accordingly, in the preferred embodiments of the invention, polypeptides that are useful in combination with a biodegradable polymer to promote wound healing include the following:

R R R R R R G D S P K;

G (dR) G D S P A S S K;

nMe G (dR) (dR) (dR) (dR) (dR) G G G (dR) G D S P A S S K; and

G (dR) (dR) (dR) (dR) (dR) G G G (dR) G D S P A S S K.

wherein R is the amino acid Arginine (Arg); dR is the amino acid D-Arginine (D-Arg); G is the amino acid Glycine (Gly); D is the amino acid Aspartic acid (Asp); S is the amino acid Serine (Ser); P is the amino acid Proline (Pro); K is the amino acid Lysine (Lys); A is the amino acid Alanine (Ala); and nMe is an n-methyl group.

These peptides are synthetic, relatively easy to manufacture (as compared, for example, to fibronectin) and do not need to be extracted from blood. In addition, the smaller size of the peptide (as compared, for example, to fibronectin) allows many more binding sites to be attached to a given volume of biodegradable polymer. These peptides are also much more stable than fibronectin in solution. In particular, D-Arg confers protease resistance. Moreover, because they do not carry species-specific immunological determinants, they can therefore be used in both veterinary and human applications. Preferably such peptides contain at least one group of at least three amino acids selected from the D or L forms of Arg, Lys, or ornithine to the N terminal side of the Arg-Gly-Asp sequence.

A preferred biodegradable polymer of the invention is hyaluronic acid. Hyaluronic acid consists of alternating residues of D-glucuronic acid and N-acetyl-D-glucosamine. The polymer is found in the dermal matrix and is commercially available from many sources in pure form. It can form gels or viscous solutions because it is a water soluble polymer. Other gel forming biodegradable polymers that can be advantageously used include, but are not limited to, collagen, agarose, starch. The polymers may be cross-linked to stabilize their physical properties.

An alternatively preferred biodegradable polymer particularly for opthalmic applications, is chondroitin sulfate, due to its ability to specifically bind exposed collagen/matrix. Such conjugates form stable solutions which can be provided in liquid form, such as eye drops. Other polymers that can be advantageously used include heparin, heparan sulfate, dextran, polylactate and polyglycolic acid. In addition, these materials could be used in dermal application by crosslinking them to form a gel, or by forming mesh-like structures.

The two components of the wound healing conjugate can be joined by a number of procedures. Preferably, they are joined using 1-ethyl-3-3-dimethylaminopropylcarbodiimide (EDC), a cross-linking/coupling agent. Other cross-linking/coupling reagents can also be used such as dicyclohexylcarbomide (DCC), glutaraldehyde, cyanogen bromide or N-hydroxysuccinimide. Other methods, well known in the art, can alternatively be used.

A peptide-hyaluronic acid conjugate forms a semi-gel the viscosity of which can be altered by the addition of unconjugated hyaluronate or varying the degree of peptide conjugate. The semi-gel can be placed directly in a wound to aid in healing by providing an artificial biodegradable matrix. Growth factors, such as TGF-β or platelet-derived growth factor (PDGF) may be used along with the conjugate to further spur healing. In alternative embodiments the conjugate can be coated on a biodegradable mesh or other implanted material, or can itself be formed into sheets or other structures, or can be provided as a stable solution. Such conjugates can be used on any wounds which involve body tissues being cut, abraded or otherwise damaged. Such wounds include chronic skin ulcers, burns, corneal wounds and incisions. Regeneration of tissue (such as cartilage, bone, or nervous tissue) can also be enhanced by applying the conjugate.

The following examples are intended to more clearly illustrate aspects of the invention, but are not intended to limit the scope thereof.

EXAMPLE I

Peptide Synthesis

The peptide G (dR) (dR) (dR) (dR) (dR) G G G (dR) G D S P A S S K was synthesized using an automated peptide synthesizer (Model 430A; Applied Biosystems, Foster City, Calif.) according to the directions provided by the manufacturer. After cleavage from the resin with hydrogen fluoride, the peptides were washed in cold ethyl ether and precipitated from solution in trifluoroacetate with ice cold ether. The peptides where then redissolved in distilled water and lyophilized. The peptides were further purified by HPLC using a Waters Bondapak™ $C_{18}$ (3×30 cm; 10 $\mu$m packing, Waters Assoc., Milford, Mass.). Other peptides can be made by the same method.

EXAMPLE II

Preparation of Peptide-Hyaluronic Acid Conjugate

Conjugates were made by mixing a solution of hyaluronic acid, (Genzyme, Boston, Mass.) buffered in phosphate buffered saline, with the coupling agent 1-ethyl-3,3 dimethylaminopropyl carbodiimide at a concentration of 0.07M for 30 minutes. After this time, the peptide of Example I was added at a weight equal to that of the hyaluronate. This mixture was shaken overnight, after which the product was purified by dialysis and precipitation with 3 volumes acetone or ethanol. Typical preparations consisted of a conjugate containing between 20 and 30% peptide by weight. Addition of sterile phosphate buffered saline results in clear solutions, the viscosity of which can be adjusted by the addition of uncoupled hyaluronate.

EXAMPLE III

Preparation of a Chondroitin Sulfate Conjugate

The peptide of Example I was conjugated to chrondoitin sulfate by mixing chondroitin sulfate (Hepar Industries, Inc., Franklin, Ohio) at 100 mg/ml in water with 1-ethyl-3-3 dimethylaminopropylcarbodiimide (EDC) at 70 mM for 30 minutes, followed by addition of the peptide of Example I at 10 mg/ml and shaking overnight at room temperature. Conjugates were then precipitated by the addition of NaCl to 1% and 3 volumes of acetone, followed by centrifugation for five minutes at 2000×G. The conjugate was then dried under vacuum, and resuspended in phosphate buffered saline to 100 mg/ml. Typical peptide incorporation was 74 mg peptide/g conjugate. Chondroitin sulfate resulted in attachment at the level of 700 to 1000 cells/mg conjugate, determined as described in Example IV.

EXAMPLE IV

Production of Peptide Conjugates With Various Biopolymers

The peptide as prepared in Example I was conjugated to potato starch using the cyanogen bromide activation method as follows: 25 mg. CNBr was dissolved in 20 ml $H_2O$. The pH was raised quickly to pH 11 with 1NaOH, at which time 500 mg Potato Starch ( Sigma Chem. Co., St. Louis, Mo.) was added. The pH was maintained at 11 for 3, 6 or 12 minutes (by addition of additional NaOH and with constant stirring) at which time the starch was collected on filter paper (Whatman No. 2) and washed with cold water and acetone. 200 mg of these activated samples were added to 10 ml coupling buffer (0.2 M sodium bicarbonate, pH 9.5) containing 20 mg of the peptide YAVTGRGDSPASSKPIS-NYRTELLDKPSQM and stirred overnight in the cold. In the morning, conjugates were collected on Whatman #2 filter paper, washed with coupling buffer, 0.01N HCl, 1 M NaCl, and graded water/acetone (80%, 60%, 40%, 20%), then acetone. Peptide incorporation was assayed by ninhydrin assay. Yield was approximately 10 mg peptide incorporated/g starch.

Alternatively, the peptide were conjugated to potato starch using dicyclohexylcarbodiimide (DCC) activation. 0.2 g potato starch was suspended in6 ml dioxane, 100 $\mu$g DCC was added, and the mixture shaken for 30 minutes. The starch was then collected on a fritted glass filter, and washed with dioxane. After air drying, it was added to 8 ml of 1M $Na_2CO_3$, pH 10, 1.2 mg peptide was added, and the mixture shaken overnight at 4° C. In the morning, conjugates were collected by filtration, washed with water, 1 M NaCl, water and graded acetone/water as before. Peptide incorporation was assayed by ninhydrin. Typical yields were 3 to 4 mg peptide incorporated/g potato starch.

The peptide was also conjugated to agarose (Bethesda Research Laboratories, Gaithersburg, Md.) as by the above diacylohexylcarbodiimide activation method using 40 $\mu$g of DCC in place of 100 $\mu$g of DCC.

A pepetide prepared by the method of Example I was conjugated to Sepharose ® according to a modification of the method of Pierschbacher and Ruoslahti (Nature 309: 30–33 (1984), which is incorporated herein by reference. 50 mg of Sepharose in 7.5 ml 1M $Na_2CO_3$ was activated with 20 mg CNBr for 10 minutes. After collection and washing, the samples were resuspended in 5 ml 1M $Na_2CO_3$, and shaken with 1 mg of the peptide GRGDSPK overnight in the cold. The conjugates were then collected and washed as before, and peptide incorporation assayed by BCA protein assay (Pierce Chemical Co.) using peptide as standard. Incorporation was at the level of 5 mg/ml beads.

These conjugates were tested for cell attachment by immobilizing them onto tissue culture plastic coated with 100 $\mu$g/ml rabbit immunoglobulin G. This was done through the addition of the conjugate to the well, followed by the addition of concentrated 1-ethyl-3-3-dimethylaminopropylcarbodiimide (EDC) to couple the conjugate to the protein coating. After 4 hours, the wells were washed, and cells (normal rat kidney cells at $2\times10^5$/ml) added and incubated for 1 hour at 37° C. After fixation and staining, cell attachment was assayed.

All conjugates showed peptide-dependent cell attachment; there was little or no cell attachment to the biopolymer alone but significant cell attachment to the peptide-biopolymer conjugate. The potato starch conjugates resulted in binding of approximately 150 cells/mg conjugated starch gel.

EXAMPLE V

Measurement of Wound Strength and Healing After Treatment with Peptide-Hyaluronate Conjugates Wistar Furth adult male rats (175–250g) were anesthetized by intraperitoneal injection of pentobarbital (60 mg/kg body weight). The rats dorsal area was closely shaved, and each animal was positioned and secured for surgery. Using aseptic technique, five full thickness skin incisions, 1.5 cm long, were made on the dorsal area. Each incision was treated with 0.05–0.10 ml of a blind sample of the peptide RRRRRRGDSPK-conjugated to hyaluronate or with 0.05–0.10 ml of human fibronectin (3 mg/ml in PBS, Colloborative Research, Bedford, Mass.) or rat fibronectin (2 mg/ml in PBS, Telios Pharmaceuticals, San Diego, Calif.) or was left untreated as a control. After treatment, the incisions were closed using standard 4-0 nylon sutures for placement of 5 to 7 interrupted sutures. The rats were returned to their cages for recovery and observation. At post operative days 2 through 7 and 10, six animals were anesthetized as above and were euthanized by an intracardiac injection of 0.5 cc of T-61.

Figure 1:
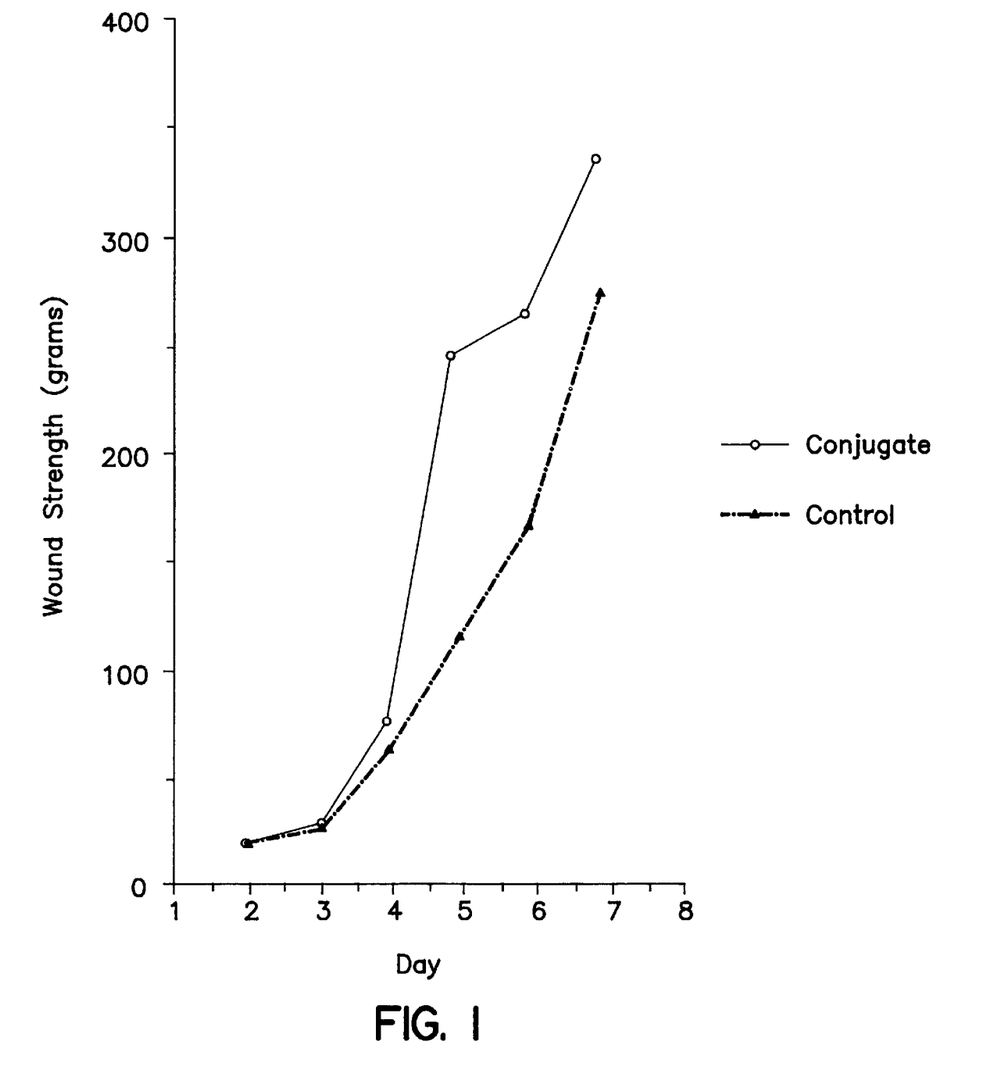
FIG. 1 shows the wound strength gains made using the conjugate hyaluronate and $R_6GDSPK$ over a ten day test as compared with the control.
Figure 2:
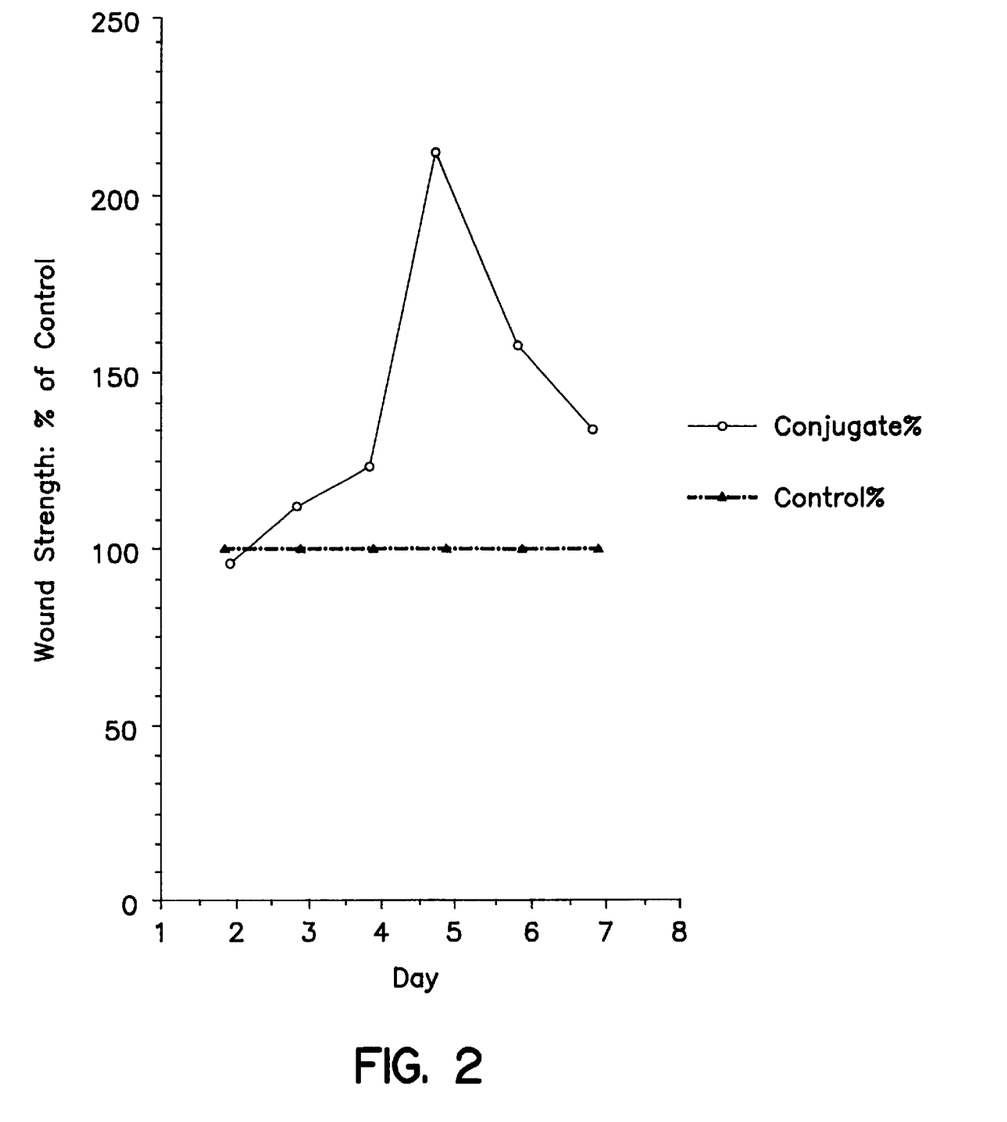
FIG. 2 shows the results of FIG. 1 as a percentage of the control.

Following euthanasia, the pelt was removed from the rat and 5 mm wide by 2 cm long skin strips bisecting incisions were prepared. Histological specimens from the skin adjacent to the tensile strength strip were also taken. To measure tensile strength, one end of the strip was clipped using a 1 mm Michel Clipper (Militex Instruments Co.) which was tied to a Grass model FTO3C force displacement transducer. The other end of the strip was clipped using a light weight hemostat which was attached to a Harvard Model 901 push-pull infusion pump (Harvard Instruments, Millis, Mass.) using cotton thread over a pulley. The transducer was attached to a Grass polygraph (Model 7D) for recording the results. After calibration, the pump was turned on to pull at the rate of 64 mm/min. The amount of force required to pull the skin apart at the incision was recorded on the polygraph. The results are shown in FIGS. 1 and 2. As these Figures show, wound strength was increased by use of the conjugate for days 3 through 7 after incision, with the maximum effect being seen at day 5, where the conjugate-treated wounds achieved 211% of the strength of untreated wounds.

EXAMPLE VI

Testing of Peptide-Hyaluronate Conjugates in a Polyvinylalcohol Sponge Implant Model Peptide-hyaluronate conjugates were tested using the model of Davidson, et al., J. Cell Biol. 100: 1219–1227 (1985), which is incorporated herein by reference. This model involves the implantation of inert PVA sponges loaded with the conjugates or control materials under the skin of rats. The sponges were removed from the animals at 4 to 10 days after implantation and analyzed for cell ingrowth number and type and as collagen content, blood vessel formation (angiogenesis) and inflammatory response, as well as persistence of the conjugate in the wound. Results of these studies indicated:

A. Sponges containing hyaluronate conjugated with the peptide $R_6$GDSPK by the method of Example II give rise to increased angiogenesis, collagen secretion and fibroblast migration at early time points, with the effect diminishing at later time points, such that the sponge appeared similar to the control sponges by the end of the experiment, except that more collagen was continuously deposited into the sponges loaded with hyaluronate-peptide conjugates.

B. Hyaluronate conjugate slowly disappeared from the sponge, with markedly less conjugate present by 14 days after implantation.

EXAMPLE VII

Testing of Peptide-Hyaluronate Conjugates in Rat Dermal Incisions

Figure 3:
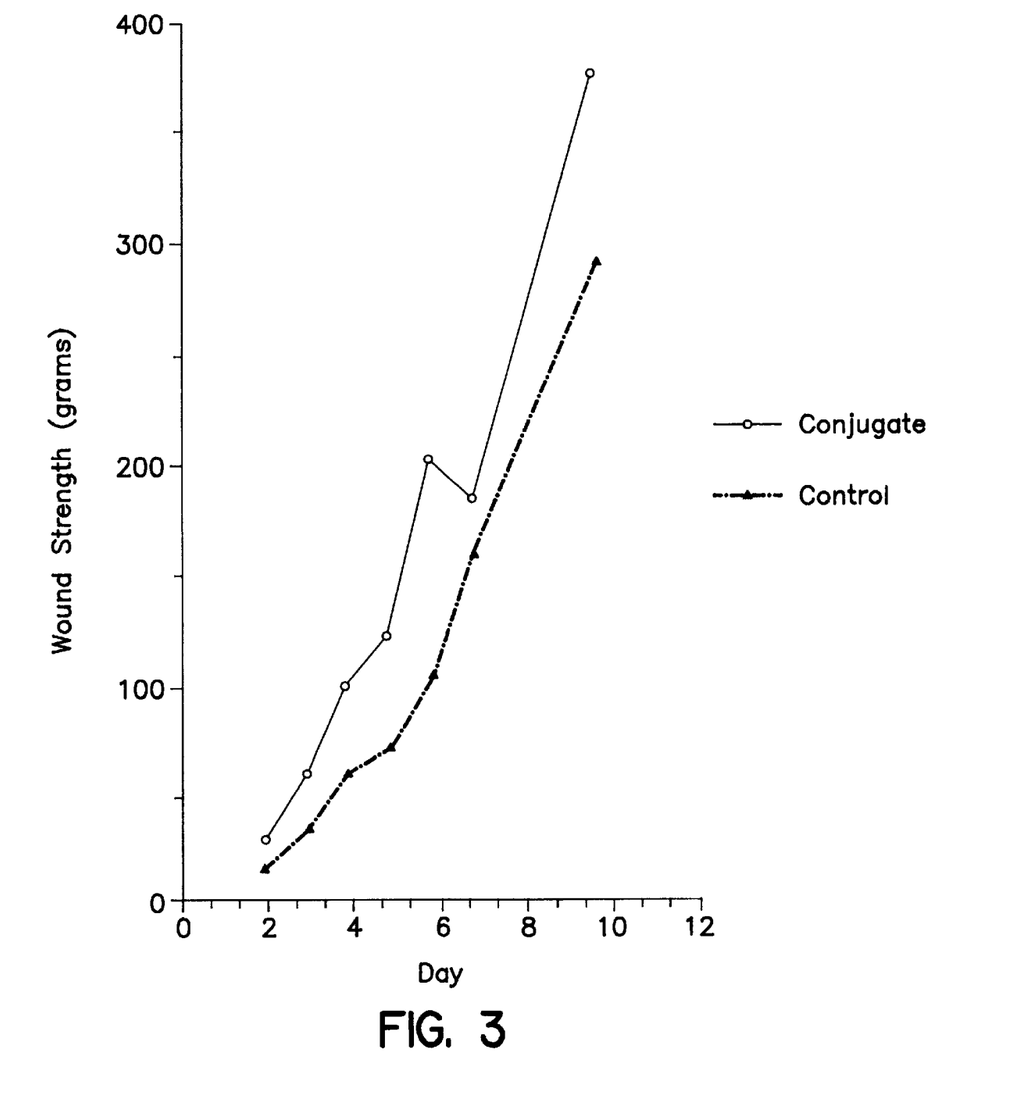
FIG. 3 shows the results of the second wound strength experiment using conjugate of hyaluronate—$G(dR)_5G_3(dR)$GDSPASSK
Figure 4:
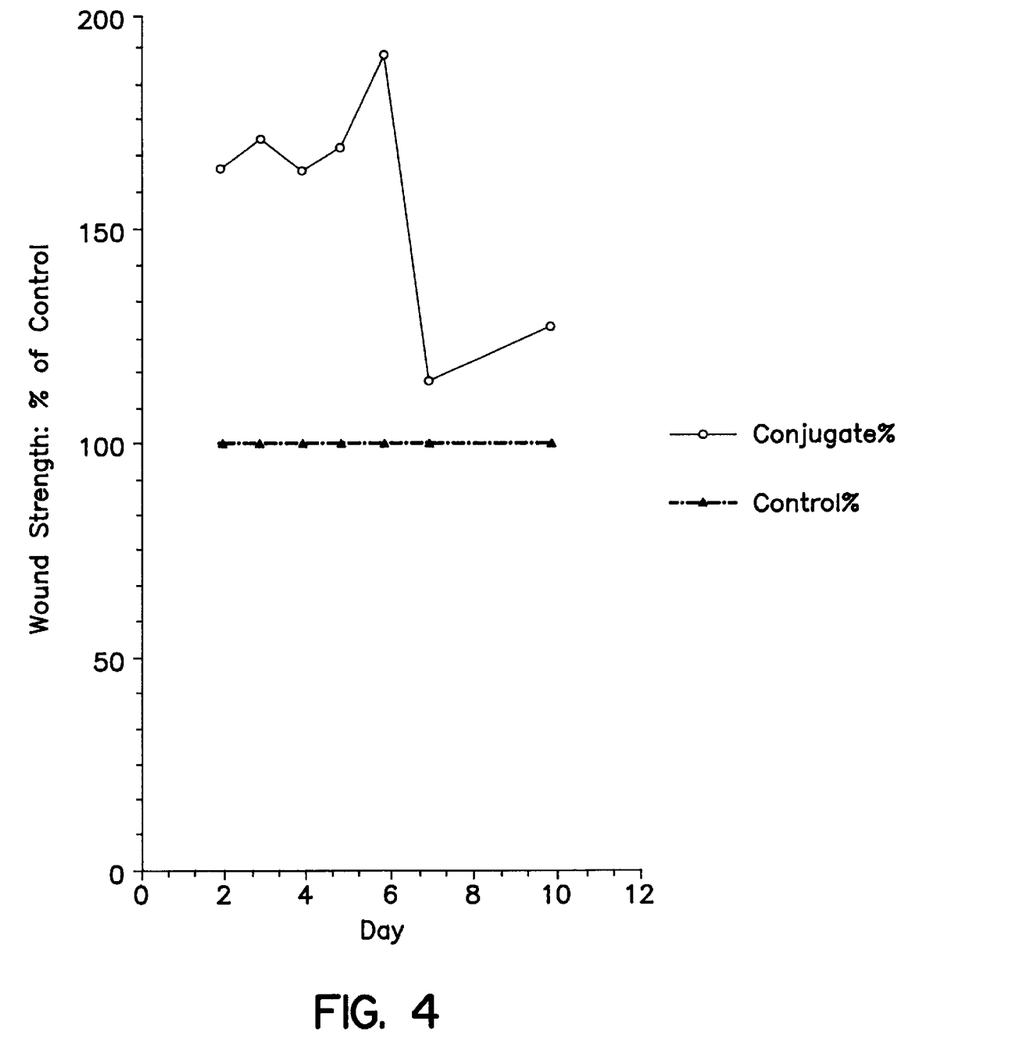
FIG. 4 shows the data of FIG. 3 as a percent of the control wounds.

The methods of Example V were used to test whether the conjugates employing the peptide $G(dR)_5G_3(dR)$GDSPASSK (found to have more activity than the RGGD-SPK peptide conjugate tested in Example V in in vitro assays of the type described in Pierschbacher, et al., Natl. Acad. Sci. 80: 1224—1227, (1983) also had superior activity in vivo. As can be seen in FIGS. 3 and 4, conjugates of this peptide showed earlier activity (attaining 160% of control on day 2) and persistent activity (maintaining activity greater than control through day 10).

EXAMPLE VIII

Treatment of Dry Eye Syndrome with Chondroitin-Sulfate Peptide Conjugates

The dry eye conditon was induced in six cats on day zero by the excision of tear ducts from the eyes. The cats were divided into two groups and treated as follows:

Group one was treated with two drops of human fibronectin, 3 mg/ml, a day twice a day from day 17 to day 34, and two drops a day three times a day from day 34 to 43. Group two was treated with two drops of chondroitin sulfate-peptide conjugate, $G(dR)_5G_3(dR)$GDSPASSK 100 mg/ml, a day twice a day from days 17 to 34, and two drops a day three times a day from day 34 to day 43.

Eyes were examined by impression cytology, in which an impression of the surface of the eye is taken by the placement of a polymer on the eye surface and the cells stuck to the surface examined microscopically, and by staining the eyes with rose bengal, a reddish stain which selectively stains the exposed matrix and underlying basal epithelial cells but does not stain undamaged corneal epithelium.

Cats in Group 2, treated with the peptide conjugate, exhibited marked reduction of the dry eye condition. Cats treated with chondroitin sulfate alone and untreated cats did not show any change over the time shown.

Although the invention has been described with reference to the presently preferred embodiments, it should be understood that various modifications can be made by those skilled in the art without departing from the invention. Accordingly, the invention is set out in the following claims.

We claim:

1. A synthetic matrix consisting of:
   a) a synthetic polypeptide comprising the amino acid sequence dArg-Gly-Asp, said polypeptide having cell attachment promoting activity and less than about 30 amino acids; and
   b) a biodegradable polymer bonded to said polypeptide without substantially reducing said cell attachment promoting activity of said polypeptide, wherein said polymer is selected from the group consisting of hyaluronic acid, chondroitin sulfate, heparin, heparin sulfate, polylactate, and polyglycolic acid; and
   c) optionally a crosslinking agent; wherein said synthetic matrix promotes cell attachment and migration therein and is not a solid support.

2. A synthetic matrix consisting of:
   a) a synthetic polypeptide comprising the amino acid sequence G(dR)(dR)(dR)(dR)(dR)GGG(dR)GDSPASSK, said polypeptide having cell attachment promoting activity; and
   b) a biodegradable polymer bonded to said polypeptide without substantially reducing said cell attachment promoting activity of said synthetic polypeptide, wherein said polymer is hyaluronic acid; and
   c) optionally a crosslinking agent; wherein said synthetic matrix promotes cell attachment and migration therein and is not a solid support.

3. A synthetic matrix consisting of:
   a) a synthetic polypeptide comprising amino acid sequence G(dR)(dR)(dR)(dR)GGG(dR)GDSPASSK, said polypeptide having cell attachment promoting activity; and
   b) a biodegradable polymer bonded to said polypeptide without substantially reducing said cell attachment promoting activity of said polypeptide, wherein said polymer is chondroitin sulfate; and
   c) optionally a crosslinking agent; wherein siad synthetic matrix promotes cell attachment and migration therein and is not a solid support.

4. The synthetic matrix of claim 1, wherein said synthetic polypeptide further comprises at least one group of at least three identified amino acids in sequence selected from K, dK, dR, ornithine or D-ornithine.

5. The synthetic matrix of claim 1, wherein said synthetic polypeptide has the amino acid Lysine (K) at its C-terminus.

6. The synthetic matrix of claim 1, wherein said synthetic polypeptide is selected from the group consisting of:
   G (dR) G D S P A S S K;
   nMe G (dR) (dR) (dR) (dR) (dR) G G G (dR) G D S P A S S K;
   G (dR) (dR) (dR) (dR) (dR) G G G (dR) G D S P A S S K; and synthetic polypeptides containing any of the above sequences.

7. The conjugate of claim 1, wherein said biodegradable polymer comprises hyaluronic acid.

8. The conjugate of claim 1, wherein said biodegradable polymer comprises chondroitin sulfate.

9. The synthetic matrix of claim 2 wherein the synthetic matrix contains a cross linking agent selected from the group consisting of 1-ethyl-3-3-dimethyl-aminoproplycarbodimide, dicyclohexylcarbomide, glutaraldehyde, cyanogen bromide and N-hydroxysucinimide.

10. The synthetic matrix of claim 3 wherein the synthetic matrix contains a cross linking agent selected from the group consisting of 1-ethyl-3-3-dimethyl-aminoproplycarbodimide, dicyclohexylcarbomide, glutaraldehyde, cyanogen bromide and N-hydroxysucinimide.

* * * * *

UNITED STATES PATENT AND TRADEMARK OFFICE
CERTIFICATE OF CORRECTION

PATENT NO.    : 5,955,578
DATED         : September 21, 1999
INVENTOR(S)   : Pierschbacher et al.

It is certified that error appears in the above-identified patent and that said Letters Patent is hereby corrected as shown below:

Column 1,
Line 21, please delete "in may" and replace with -- in many --.

Signed and Sealed this

Twenty-third Day of July, 2002

Attest:

Attesting Officer

JAMES E. ROGAN
Director of the United States Patent and Trademark Office